(12) United States Patent
Abe et al.

(10) Patent No.: US 8,084,201 B2
(45) Date of Patent: Dec. 27, 2011

(54) FLUORESCENT MOLECULE

(75) Inventors: Hiroshi Abe, Saitama (JP); Yoshihiro Ito, Tokyo (JP); Kazuhiro Furukawa, New Haven, CT (US)

(73) Assignee: Riken, Saitama (JP)

( * ) Notice: Subject to any disclaimer, the term of this patent is extended or adjusted under 35 U.S.C. 154(b) by 0 days.

(21) Appl. No.: 12/677,014

(22) PCT Filed: Aug. 1, 2008

(86) PCT No.: PCT/JP2008/063871
§ 371 (c)(1),
(2), (4) Date: Sep. 22, 2010

(87) PCT Pub. No.: WO2009/034790
PCT Pub. Date: Mar. 19, 2009

(65) Prior Publication Data
US 2011/0076680 A1    Mar. 31, 2011

(30) Foreign Application Priority Data
Sep. 14, 2007  (JP) ................................ 2007-239234

(51) Int. Cl.
*C12Q 1/68* (2006.01)
*C07H 21/04* (2006.01)

(52) U.S. Cl. .......................................... 435/6; 536/26.6
(58) Field of Classification Search ...... 435/6; 536/26.6
See application file for complete search history.

(56) References Cited

U.S. PATENT DOCUMENTS
6,608,213 B1    8/2003  Sato et al.
2004/0063918 A1  4/2004  Young et al.
2005/0255475 A1  11/2005 Kumar et al.
2005/0260593 A1  11/2005 Kumar et al.
2006/0105410 A1  5/2006  Maeda et al.

FOREIGN PATENT DOCUMENTS
EP    2103616       9/2009
JP    2001-289851   10/2001
JP    2005-47898    2/2005
JP    2006-500065   1/2006
WO    2008/075718   6/2008

OTHER PUBLICATIONS

International Search Report that issued with respect to PCT/JP2008/063871, mailed Aug. 26, 2008.
International Preliminary Report on Patentability for PCT/JP2008/063871, mailed Apr. 15, 2010.
Cai et al., "Nucleic Acid-Triggered Fluorescent Probe Activation by the Staudinger Reaction," *Journal of the American Chemical Society*, vol. 126, No. 50, pp. 16324-16325, 2004.
Lemieux et al., "A Fluorogenic Dye Activated by the Staudinger Ligation," *Journal of the American Chemical Society*, vol. 125, No. 16, pp. 4708-4709, 2003.
Loubinoux et al., "Protection des Phénols par le Groupement Azidomethylene Application a la Synthése de Phénols instables," *Tetrahedron*, vol. 44, No. 19, pp. 6055-6064, 1988.
Extended European Search Report that issued with respect to European Patent Application No. 08792084.9, dated Oct. 27, 2010.

*Primary Examiner* — Jezia Riley
(74) *Attorney, Agent, or Firm* — Greenblum & Bernstein, PLC

(57) ABSTRACT

It is an object of the present invention to provide an on-off type fluorescent compound (a fluorescence-producing molecule system) used in gene analyses, which is highly stable (namely, being active for a long period of time) and highly sensitive, and which enables amplification of a trace amount of gene signal and observation thereof. The present invention provides a nonfluorescent molecule having a fluorescent substance skeleton such as fluorescein skeleton and having a group represented by —O—C(Y1)(Y2)-N$_3$ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group, in the molecule.

10 Claims, 8 Drawing Sheets

(A) Fluorescence-producing molecule system (B) Example of fluorescein derivative

[Fig.1]
(A) Fluorescence-producing molecule system
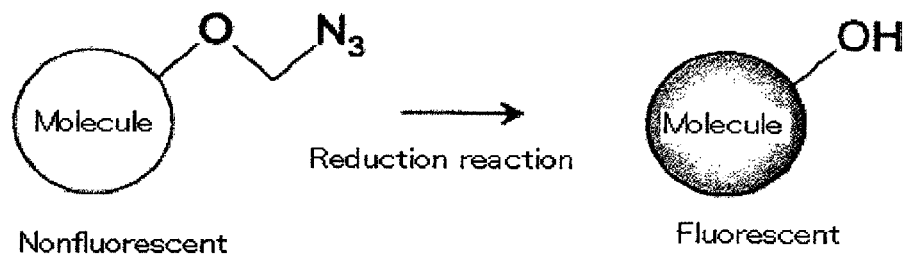
Nonfluorescent → Reduction reaction → Fluorescent
(B) Example of fluorescein derivative
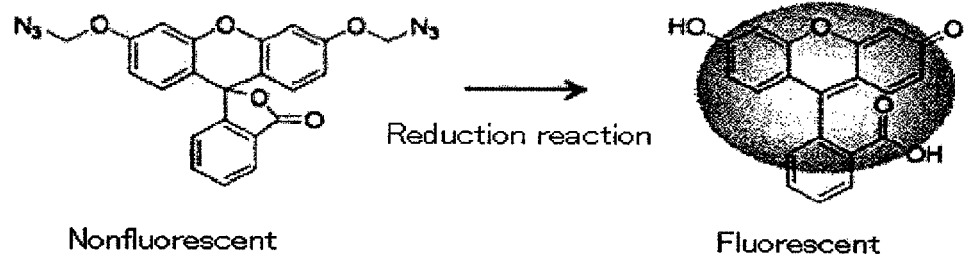
Nonfluorescent → Reduction reaction → Fluorescent

[Fig.2]
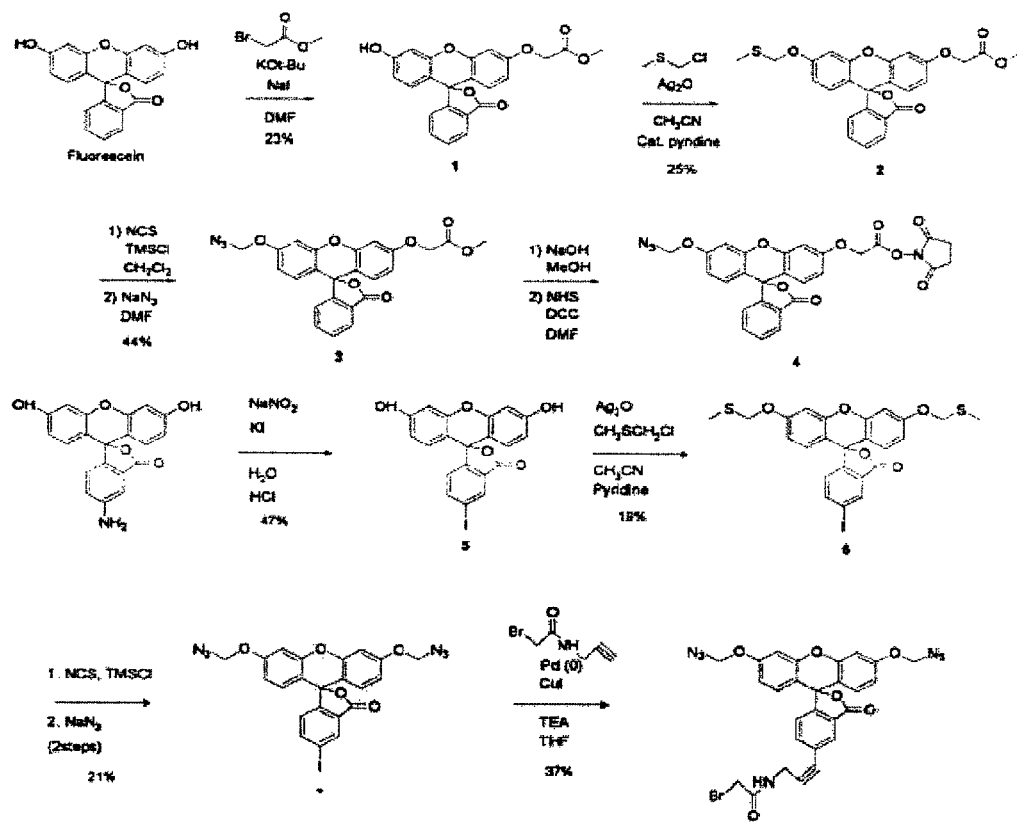

[Fig.3]
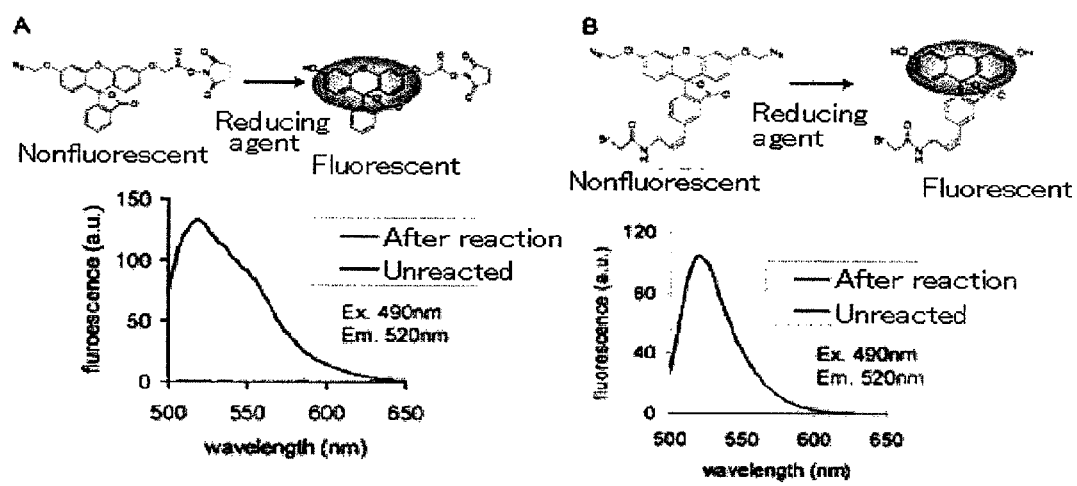

[Fig.4]
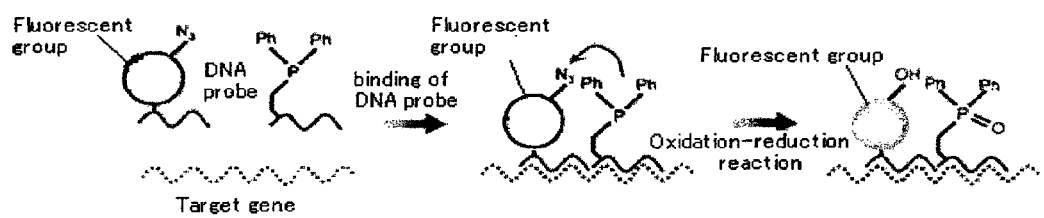
[Fig.5]
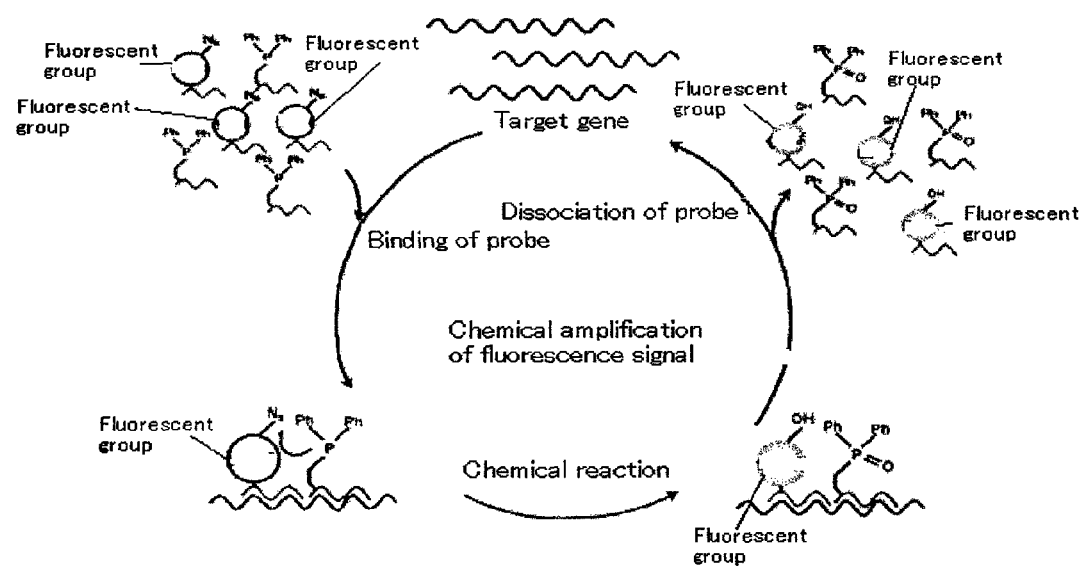

[Fig.6]
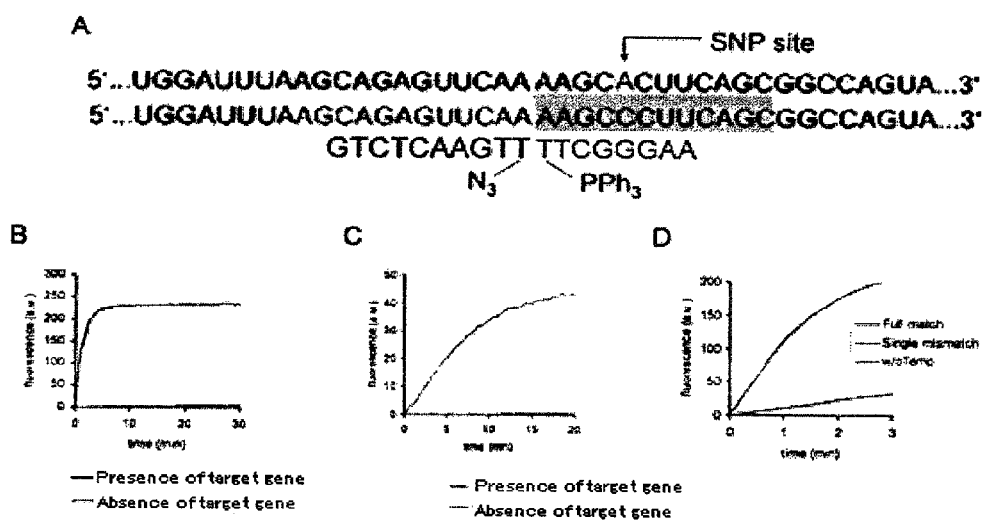

[Fig.7]
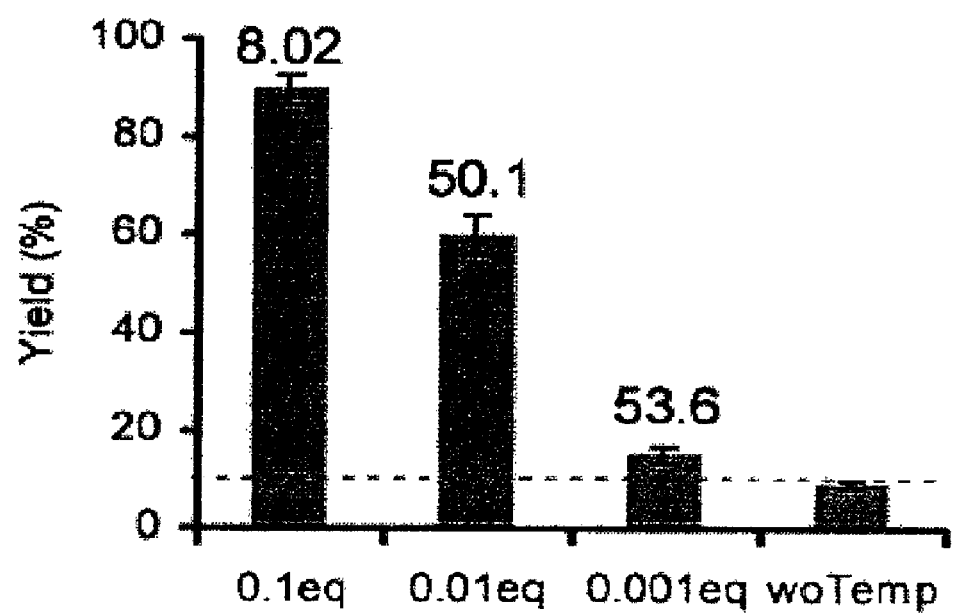

[Fig.8]
```
    TTTGAATATTTGCTA-(Az)     (TPP)-CTACCACCAAGATCT
3'  AAACUUAUAAACGAU----------GAUGGUGGUUCUAGA 5'   Target RNA
```
Probe sequence with respect to human 28S rRNA
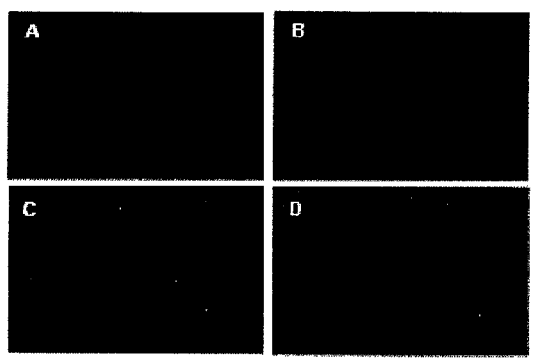
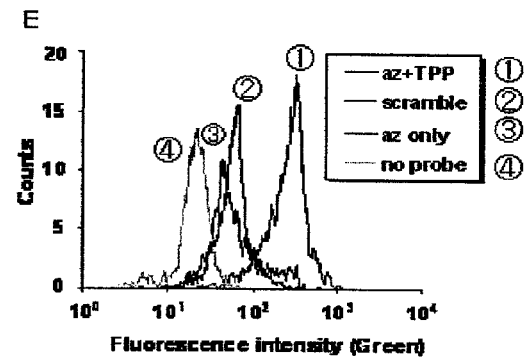

[Fig.9]
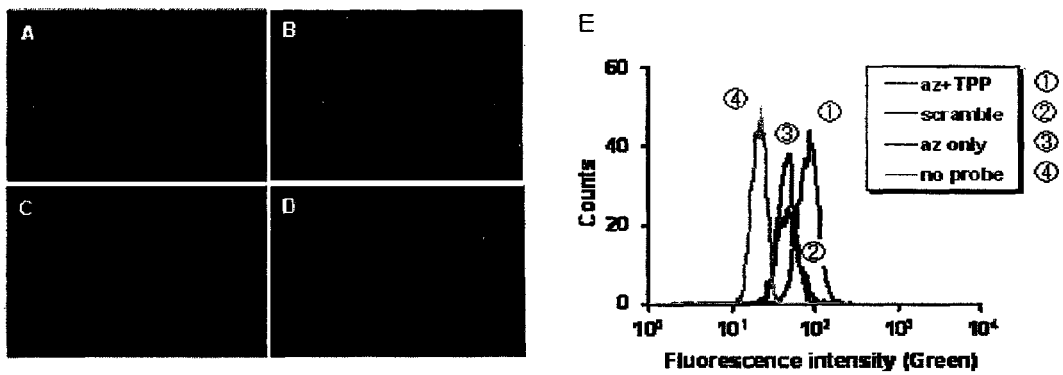

SEQUENCE LISTING

```
<160> NUMBER OF SEQ ID NOS: 21

<210> SEQ ID NO 1
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uggauuuaag cagaguucaa aagcacuuca gcggccagua                         40

<210> SEQ ID NO 2
```

-continued

<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uggauuuaag cagaguucaa aagcccuuca gcggccagua                              40

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ttgaactctg                                                              10

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
tttgaatatt tgcta                                                        15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ctaccaccaa gatct                                                        15

<210> SEQ ID NO 6
<211> LENGTH: 15
<212> TYPE: RNA
<213> ORGANISM: Homo sapiens

<400> SEQUENCE: 6
uagcaaauau ucaaa                                                        15

<210> SEQ ID NO 7
<211> LENGTH: 15
<212> TYPE: RNA
<213> ORGANISM: Homo sapiens

<400> SEQUENCE: 7
agaucuuggu gguag                                                        15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cagaggcgta caggg                                                    15

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
atagcacagc ctgga                                                    15

<210> SEQ ID NO 10
<211> LENGTH: 15
<212> TYPE: RNA
<213> ORGANISM: Homo sapiens

<400> SEQUENCE: 10
cccuguacgc cucug                                                    15

<210> SEQ ID NO 11
<211> LENGTH: 15
<212> TYPE: RNA
<213> ORGANISM: Homo sapiens

<400> SEQUENCE: 11
uccaggcugu gcuau                                                    15

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gcggcgatat catca                                                    15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
tccatggtga gctgg                                                    15

<210> SEQ ID NO 14
<211> LENGTH: 15
<212> TYPE: RNA
<213> ORGANISM: Homo sapiens

<400> SEQUENCE: 14
ugaugauauc gccgc                                                    15

<210> SEQ ID NO 15
<211> LENGTH: 15
<212> TYPE: RNA
<213> ORGANISM: Homo sapiens

<400> SEQUENCE: 15

-continued ccagcucacc augga                                               15

<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
ttcccgctcg gccgt                                               15

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
ggtggtgaag ctgta                                               15

<210> SEQ ID NO 18
<211> LENGTH: 15
<212> TYPE: RNA
<213> ORGANISM: Homo sapiens

<400> SEQUENCE: 18 acggc cgagcgggaa                                               15

<210> SEQ ID NO 19
<211> LENGTH: 15
<212> TYPE: RNA
<213> ORGANISM: Homo sapiens

<400> SEQUENCE: 19
uacagcuuca ccacc                                               15

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tggatttaag cagagttcaa aagcacttca gcggccagta                    40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tggatttaag cagagttcaa aagcccttca gcggccagta                    40

FLUORESCENT MOLECULE

TECHNICAL FIELD

The present invention relates to a fluorescence-producing molecule which is useful as a labeling reagent for detecting biologically-relevant substances such as nucleic acids. More specifically, the present invention relates to a nonfluorescent molecule having a group represented by —O—C(Y1)(Y2)-$N_3$, which is characterized in that it produces fluorescence when the above-mentioned group is reduced to a hydroxyl group or an oxo group. Furthermore, the present invention also relates to a labeling reagent comprising the aforementioned fluorescence-producing molecule and a method for detecting a target nucleic acid sequence using the aforementioned fluorescence-producing molecule.

BACKGROUND ART

As a method for detecting a nucleic acid molecule having a specific target nucleic acid sequence, a hybridization method using a probe having a nucleotide sequence complementary to the target nucleic acid sequence has been widely used. In the hybridization method, a probe having a nucleotide sequence complementary to the target nucleic acid sequence is prepared, and only a sample having a nucleotide sequence complementary to the nucleotide sequence of the probe hybridizes thereto with high selectivity. As a means for detecting a hybrid formed as a result of the hybridization, a method of labeling a probe nucleic acid with a radioisotope, a method of labeling a probe nucleic acid with a fluorescent substance, a method using a chemiluminescent reagent, and the like are used. Fluorescent substances which can be used in the labeling of a nucleic acid include fluorescein, tetramethylrhodamine, Cy3, Cy5, and the like. A fluorescent nucleic acid probe labeled with such fluorescent substance has a high background fluorescence signal. Thus, it has been difficult to carry out highly sensitive measurement using such probe.

DISCLOSURE OF THE INVENTION

Object to be Solved by the Invention

It is an object of the present invention to solve the aforementioned problems of prior art techniques. That is to say, it is an object of the present invention to provide an on-off type fluorescent compound (a fluorescence-producing molecule system) used in gene analyses, which is highly stable (namely, being active for a long period of time) and highly sensitive, and which enables amplification of a trace amount of gene signal and observation thereof. In addition, it is another object of the present invention to provide a labeling reagent for detecting a biologically-relevant substance using the aforementioned on-off type fluorescent compound.

Means for Solving the Object

As a result of intensive studies directed towards achieving the aforementioned objects, the present inventors have succeeded in synthesizing a nonfluorescent molecule having a fluorescent substance skeleton such as a fluorescein skeleton and having a group represented by —O—$CH_2$—$N_3$ in the molecule, which is characterized in that it produces fluorescence when the group represented by —O—$CH_2$—$N_3$ is reduced to a hydroxyl group or an oxo group. Moreover, the inventors have found that a first nucleic acid probe labeled with the aforementioned nonfluorescent molecule and a second nucleic acid probe labeled with a molecule having reduction action are hybridized to a target nucleic acid sequence, so as to reduce the group represented by —O—$CH_2$—$N_3$ of the nonfluorescent molecule in the first nucleic acid probe to a hydroxyl group or an oxo group, and that a target nucleic acid sequence can be detected by detecting the thus produced fluorescence. The present invention has been completed based on these findings.

The present invention provides a compound represented by the following formula (1) or (2):

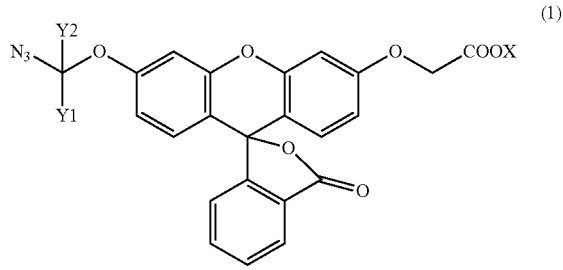

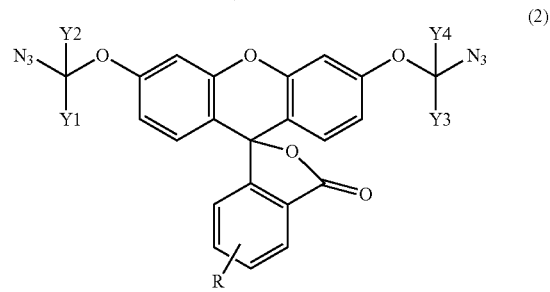

wherein X represents a hydrogen atom, or a protecting group for carboxylic acid; R represents a hydrogen atom, a halogen atom, or a reactive group that binds to a nucleic acid; and each of Y1, Y2, Y3, and Y4 independently represents a hydrogen atom, an alkyl group containing 1 to 6 carbon atoms, an alkoxy group containing 1 to 6 carbon atoms, an aryl group containing 6 to 10 carbon atoms, or a cyano group.

Another aspect of the present invention provides a labeling reagent for detecting a biologically-relevant substance, which comprises the aforementioned compound of the present invention.

Preferably, the labeling reagent of the present invention is used to label a nucleic acid.

Preferably, the labeling reagent of the present invention is used in combination with a reducing agent.

Another aspect of the present invention provides a method for detecting a target nucleic acid sequence, which comprises: a step of hybridizing to a target nucleic acid sequence, a first nucleic acid probe having a nucleic acid sequence complementary to a region of a portion of the target nucleic acid sequence, which is labeled with a nonfluorescent molecule having a skeleton selected from among a fluorescein skeleton, a xanthene skeleton, a resorufin skeleton, a coumarin skeleton, an indole skeleton and a quinazoline skeleton and having a group represented by —O—C(Y1)(Y2)-$N_3$ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group, in the molecule, and a second nucleic acid probe having a nucleic acid sequence complementary to a region of another portion of the target nucleic acid sequence, which is labeled with a molecule having reduction action; and a step of detecting a fluorescence produced by reducing the group represented by —O—C(Y1)(Y2)-$N_3$ of the nonfluorescent molecule in the first nucleic acid probe to a hydroxyl group or an oxo group.

Preferably, a nonfluorescent molecule having a fluorescein skeleton and also having a group represented by —O—C(Y1)(Y2)-$N_3$ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group in the molecule is used as said nonfluorescent molecule.

Preferably, the aforementioned compound of the present invention is used as said nonfluorescent molecule.

Preferably, the target nucleic acid sequence is RNA.

Preferably, single nucleotide polymorphism of the target nucleic acid sequence is detected.

Preferably, the target nucleic acid sequence in a cell can be detected.

Preferably, a fluorescence is detected by flow cytometry, and a cell emitting a fluorescence is selected.

Effect of the Invention

The present invention provides a fluorescence-producing molecule system using the reduction reaction of a group represented by —O—C(Y1)(Y2)-$N_3$ as a trigger. The system of the present invention can be applied to a fluorescent compound having a hydroxyl group. Moreover, the present invention provides a labeling reagent for detecting a biologically-relevant substance by applying the fluorescence-producing molecule system. The labeling reagent of the present invention binds to a target DNA or RNA molecule, so that it is reduced, and thereby it produces fluorescence. The compound of the present invention has a high signal/background ratio. Thus, it enables highly sensitive gene detection and gene detection imaging in cells or in organisms. Furthermore, it is not necessary to use other reagents or enzymes in the present invention, and this results in simplicity and low costs. It becomes possible to detect a gene, not only in a test tube, but also in a cell or in an organism. Further, the labeling agent of the present invention is highly stable (active for a long period of time) and highly sensitive, and thus it is able to amplify a trace amount of gene signal and observe it. Still further, since the labeling agent of the present invention does not need to use reagents or enzymes, it brings on simplicity and low costs, and it enables the detection of a gene, not only in a test tube, but also in a cell or in an organism.

BEST MODE FOR CARRYING OUT THE INVENTION

The embodiments of the present invention will be described in detail below.

The fluorescence-producing molecule system developed by the present invention can be generalized to an on-off type fluorescence sensor system, which produces a fluorescence as a result of the structural change of a nonfluorescent molecule triggered by reduction of a methylazido group (FIG. 1). In the examples of the present invention, a fluorescent molecule fluorescein was chemically modified, so as to synthesize a molecule, into which a methylazido group had been introduced (FIG. 2). Fluorescein was monoalkylated. Subsequently, a hydroxyl group was thiomethylated, and sodium azide or the like was further added thereto to obtain an azide. Finally, an alkyl group was converted to a succinimide, so as to obtain a monomethyl azido derivative of fluorescein (Compound 4 of FIG. 2) as a product of interest. In addition, a bismethyl azido derivative of fluorescein (Compound 8 of FIG. 2) was obtained by the same synthesis procedures (FIG. 2).

The fluorescent properties of the monomethyl azido derivative (Compound 4 of FIG. 2) and bismethyl azido derivative (Compound 8 of FIG. 2) of fluorescein were analyzed. The monomethyl azido derivative (Compound 4 of FIG. 2) and the bismethyl azido derivative (Compound 8 of FIG. 2) were both nonfluorescent compounds. These compounds were treated with reducing agents. As a result, the azido group was converted to a hydroxyl group, and a high fluorescence property was exhibited. When compared with the compounds before the treatment, fluorescence intensity was increased by a factor of approximately 300 (Compound 4 of FIG. 2) and by a factor of approximately 2600 (Compound 8 of FIG. 2) (FIG. 3).

Further, methyl azido derivatives (Compound 4 of FIG. 2) (Compound 8 of FIG. 2) that were the above synthesized fluorescence-producing molecule systems were each introduced into a nucleic acid chain to develop "chemical reaction probes" used for gene detection. The two DNA probes developed by the present invention target-sequence-specifically bind to target DNA or RNA, and they were then subjected to a chemical reaction (a reduction reaction), so that a fluorescence with high intensity can be produced (FIG. 4).

Using the presence or absence of this fluorescence signal or the intensity thereof as an indicator, a nucleic acid sequence can be distinguished or detected. The present reaction does not need other reagents or enzymes, and measurement can be carried out only by adding probes to a detection sample.

Using the probes of the present invention, an experiment was carried out to detect a leukemia gene sequence. A target DNA sequence and the synthesized probes are shown in FIG. 6A. In order to confirm target sequence-specific signal generation, a change in a fluorescence signal over time was measured even in the absence of the target sequence, and both results were then compared with each other. As a result, in the case of the present probes, such a fluorescence signal was significantly increased in the presence of the target sequence. On the other hand, such an increase in the fluorescence signal was hardly observed in the absence of the target sequence (FIG. 6B: monomethyl azido derivative (Compound 4 of FIG. 2); FIG. 6C: bismethyl azido derivative (Compound 8 of FIG. 2)). Thus, it became clear that the present probes generate a fluorescence signal in a target sequence-specific manner. Also, the present probes enabled the discrimination of single nucleotide polymorphism (SNP) (FIG. 6D).

Moreover, in the present detection reaction, a reaction cycle is rotated under isothermal conditions, so as to amplify a fluorescence signal (FIG. 5). Thus, it becomes possible to measure a trace amount of sample. Using the present probes, it becomes possible to observe gene expression in a cell or in an organism. As a matter of fact, when a target sequence concentration was decreased to create turn over conditions, a turn over number of approximately 50 could be obtained. As a result, it was found that the present fluorescence-producing system enables signal amplification of a factor of approximately 50 under isothermal conditions (FIG. 7).

The compound of the present invention (fluorescence-producing molecule) is a compound represented by the following formula (1) or (2):

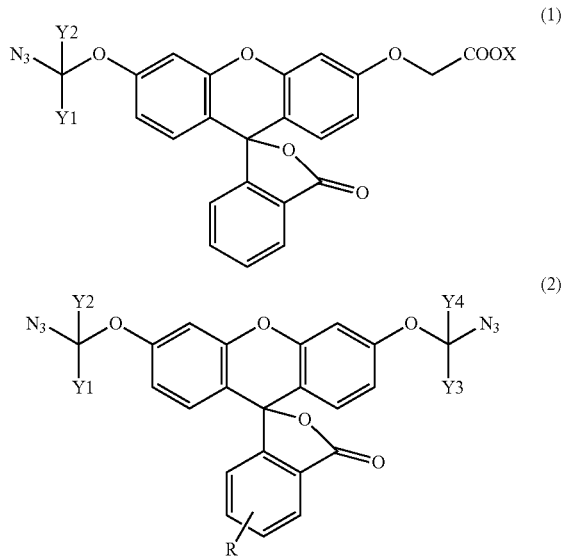

(1)

(2)

wherein X represents a hydrogen atom, or a protecting group for carboxylic acid; R represents a hydrogen atom, a halogen atom, or a reactive group that binds to a nucleic acid; and each of Y1, Y2, Y3, and Y4 independently represents a hydrogen atom, an alkyl group containing 1 to 6 carbon atoms, an alkoxy group containing 1 to 6 carbon atoms, an aryl group containing 6 to 10 carbon atoms, or a cyano group.

The type of the protecting group for carboxylic acid represented by X is not particularly limited. The protecting groups include a functional group having leaving ability, such as an alkyl group containing 1 to 6 carbon atoms, a succinimide group, an azido group, a paranitrophenyl group, and halogen.

The halogen atoms represented by R include a fluorine atom, a chlorine atom, a bromine atom, and an iodine atom.

The reactive groups that bind to a nucleic acid, represented by R, include a protected amide group, an amino group, a carboxylic acid group, an ethynyl group, halogen, an azido group, a thiol group, an aldehyde group, and the like. These groups may have an anchoring group. The protecting groups that protect an amide group include: urethane protecting groups such as a t-butoxycarbonyl group; acyl protecting groups such as a benzoyl group; alkyl protecting groups such as a trityl group; and imine protecting groups such as dimethyl acetal. As a substituent, a reactive group which can react with a nucleic acid and can bind thereto is preferable. An example of such substituent is a halogen atom. Specific examples of the reactive group that binds to a nucleic acid, represented by R, include —C≡C—CH$_2$—NHCO—CH$_2$Br, —N$_3$, —C≡CH, —SH, —NH$_2$, —CO$_2$H, and —CHO.

According to the present invention, a target nucleic acid sequence can be detected by: hybridizing to the target nucleic acid sequence, a first nucleic acid probe having a nucleic acid sequence complementary to a region of a portion of the target nucleic acid sequence, which is labeled with a nonfluorescent molecule having a skeleton selected from among a fluorescein skeleton, a xanthene skeleton, a resorufin skeleton, a coumarin skeleton, an indole skeleton and a quinazoline skeleton and having a group represented by —O—C(Y1)(Y2)-N$_3$ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group in the molecule, and a second nucleic acid probe having a nucleic acid sequence complementary to a region of another portion of the target nucleic acid sequence, which is labeled with a molecule having reduction action; and detecting a fluorescence produced by reducing the group represented by —O—C(Y1)(Y2)-N$_3$ of the nonfluorescent molecule in the first nucleic acid probe to a hydroxyl group or an oxo group.

Specific structures of a fluorescein skeleton, a xanthene skeleton, a resorufin skeleton, a coumarin skeleton, an indole skeleton and a quinazoline skeleton will be shown below.

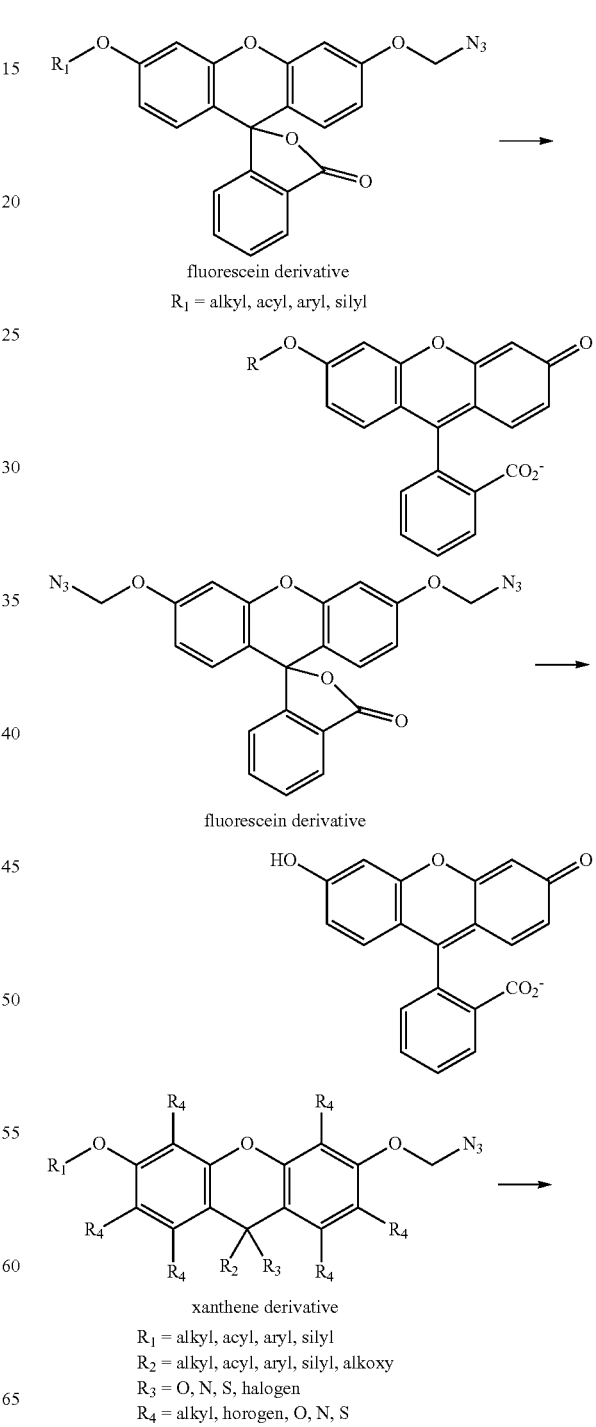

fluorescein derivative
R$_1$ = alkyl, acyl, aryl, silyl fluorescein derivative xanthene derivative
R$_1$ = alkyl, acyl, aryl, silyl
R$_2$ = alkyl, acyl, aryl, silyl, alkoxy
R$_3$ = O, N, S, halogen
R$_4$ = alkyl, horogen, O, N, S

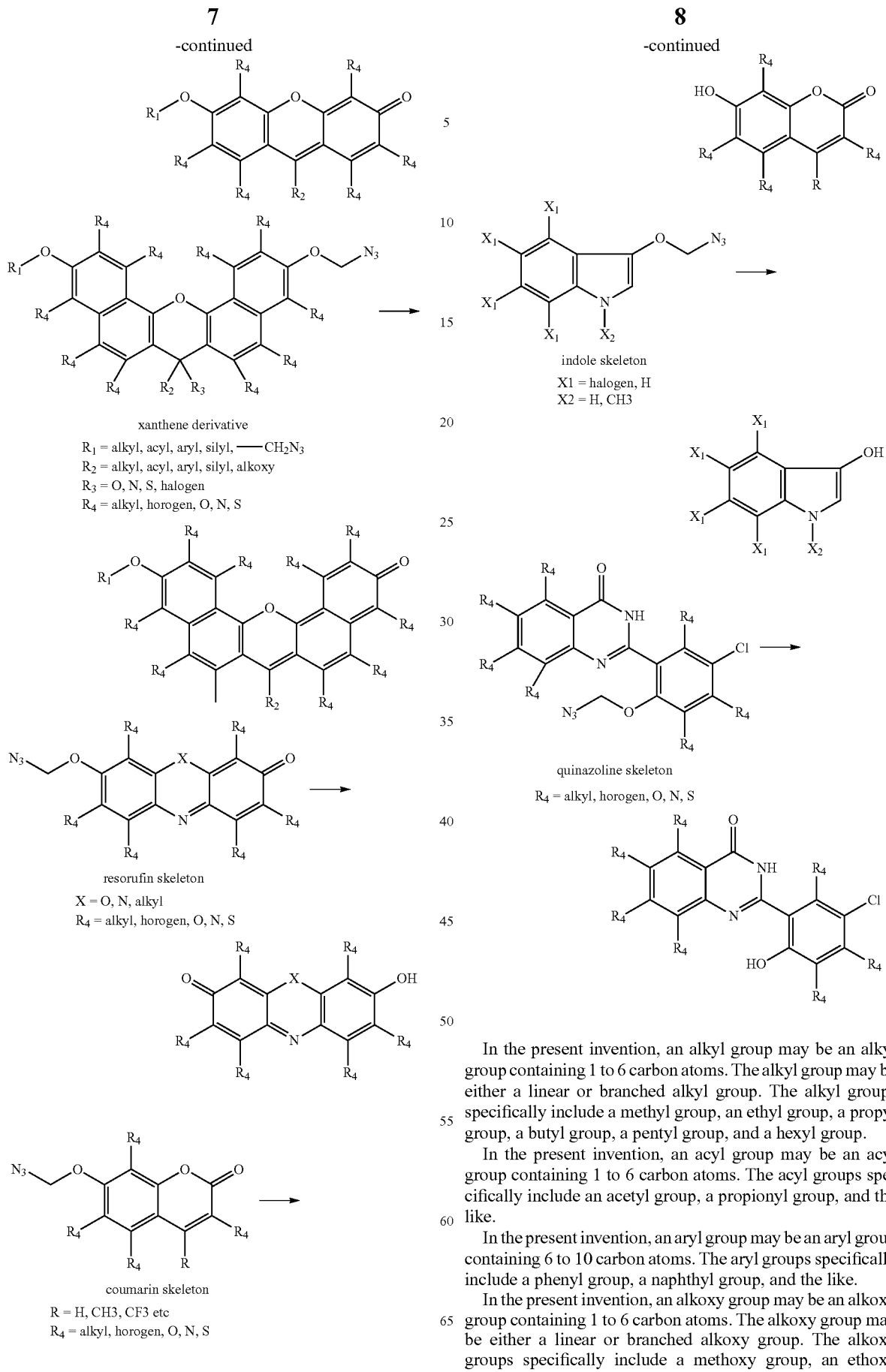

In the present invention, an alkyl group may be an alkyl group containing 1 to 6 carbon atoms. The alkyl group may be either a linear or branched alkyl group. The alkyl groups specifically include a methyl group, an ethyl group, a propyl group, a butyl group, a pentyl group, and a hexyl group.

In the present invention, an acyl group may be an acyl group containing 1 to 6 carbon atoms. The acyl groups specifically include an acetyl group, a propionyl group, and the like.

In the present invention, an aryl group may be an aryl group containing 6 to 10 carbon atoms. The aryl groups specifically include a phenyl group, a naphthyl group, and the like.

In the present invention, an alkoxy group may be an alkoxy group containing 1 to 6 carbon atoms. The alkoxy group may be either a linear or branched alkoxy group. The alkoxy groups specifically include a methoxy group, an ethoxy group, a propoxy group, a butoxy group, a pentyloxy group, a hexyloxy group, and the like.

In the present invention, halogen atoms include a fluorine atom, a chlorine atom, a bromine atom, and an iodine atom.

The first nucleic acid probe used in the present invention is labeled with a nonfluorescent molecule having the aforementioned skeleton and having a group represented by —O—C(Y1)(Y2)-$N_3$ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group, in the molecule.

The second nucleic acid probe used in the present invention is labeled with a molecule having reduction action. The molecules having reduction action that can be used in the present invention include a sulfur compound, a trivalent phosphorus compound, and the like. An example of the sulfur compound is DTT (dithiothreitol). Examples of the trivalent phosphorus compound include triphenylphosphine and alkylphosphine.

In the present invention, the first nucleic acid probe has a nucleic acid sequence complementary to a region of a portion of the target nucleic acid sequence, and the second nucleic acid probe has a nucleic acid sequence complementary to a region of another portion of the target nucleic acid sequence. Herein, the region of the target nucleic acid sequence recognized by each of the first nucleic acid probe and the second nucleic acid probe can be arbitrarily determined, as long as it satisfies conditions in which, when both of the above probes hybridize to the target nucleic acid sequence, the group represented by —O—C(Y1)(Y2)-$N_3$ of the nonfluorescent molecule in the first nucleic acid probe is reduced to a hydroxyl group or an oxo group by the action of the molecule having reduction action in the second nucleic acid probe. In order to satisfy the aforementioned conditions, in general, the regions of the target nucleic acid sequence recognized by the first nucleic acid probe and the second nucleic acid probe are preferably adjacent to or close to each other. The regions of the target nucleic acid sequence recognized by the first nucleic acid probe and the second nucleic acid probe are preferably close to each other across a space consisting of approximately 1 to 10 nucleotides.

The present invention will be more specifically described in the following examples. However, these examples are not intended to limit the scope of the present invention.

EXAMPLES

Example 1

Organic Synthesis of Monomethyl Azido Derivative of Fluorescein (1) Synthesis of Monoalkyl Fluorescein (Compound 1 of FIG. 2)

Fluorescein (3.00 g, 9.03 mmol) and sodium iodide (271 mg, 1.81 mmol) were dissolved in DMF (50 ml) under ice bath cooling, and potassium t-butoxide (3.04 g, 27.1 mmol) dissolved in THF (30 ml) was then added to the solution. After the solution had become transparent, methyl bromoacetate (944 μl, 9.94 mmol) was slowly added thereto, and while gradually returning the reaction solution to room temperature, the mixture was stirred for 2.5 hours. Thereafter, the reaction was terminated with EtOAc, and liquid separation was then carried out using $H_2O$ and brine. An organic layer was dried over $Na_2SO_4$, and the residue was then purified by flash column chromatography (silica, gradient elution 30:1 $CHCl_3$/MeOH to 20:1 $CHCl_3$/MeOH with 0.5% triethylamine). The obtained monoalkyl fluorescein (Compound 1 of FIG. 2) was in the form of a transparent liquid (820 mg, 23%).

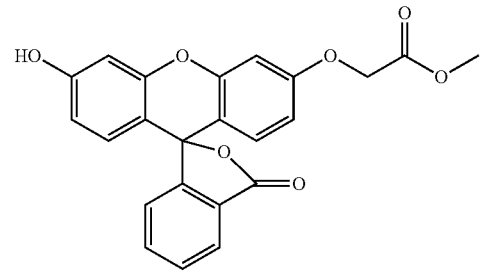

1H NMR (400 MHz, $CD_3OD$) δ7.91 (1H, d, J=7.32 Hz), 7.62 (2H, dt, J=16.40, 15.10 Hz), 7.10 (1H, d, J=7.56 Hz), 6.79 (1H, d, J=2.20 Hz), 6.67-6.55 (4H, m), 6.44 (1H, dd, J=2.20, 2.44 Hz), 4.70 (2H, s), 3.69 (3H, s),

13C NMR (100 MHz, $CD_3OD$) δ 180.6, 172.5, 169.9, 163.5, 159.4, 155.1, 138.8, 137.6, 129.6, 129.1, 124.9, 116.3, 116.0, 114.5, 104.7, 102.3, 66.1, 52.7

QSTAR (Applied Biosystems/MDS SCIEX) (ESI): m/z 404.0896 [MH+] C23H16O7: 405.0974, found: 405.0987

(2) Synthesis of Monoalkyl Thiomethyl Fluorescein (Compound 2 of FIG. 2)

The monoalkyl fluorescein (Compound 1 of FIG. 2) (720 mg, 1.78 mmol) was dissolved in anhydrous $CH_3CN$ (36 ml) in an Ar atmosphere. Silver oxide (620 mg, 2.67 mmol), chloromethyl methyl sulfide (223 μl, 2.67 mmol) and five drops of pyridine were added to the reaction solution, and the obtained mixture was then stirred at 40° C. for 15 hours. Thereafter, the reaction solution was filtrated with Celite and was concentrated, and the resultant was then purified by flash column chromatography (hexane/AcOEt from 6:1 to 2:1 (v/v) with 0.5% triethylamine). The obtained monoalkyl thiomethyl fluorescein (Compound 2 of the FIG. 2) was in the form of a yellow crystal (206 mg, 25%).

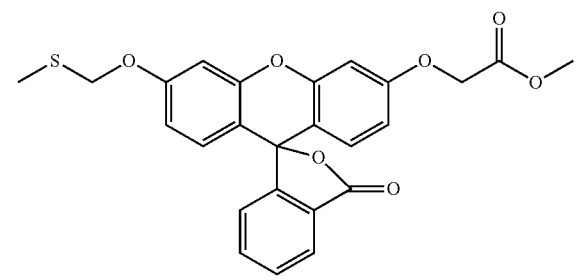

1H NMR (400 MHz, CDCl3) δ8.01 (1H, d, J=7.08 Hz), 7.64 (2H, dt, J=16.10, 15.10 Hz), 7.15 (1H, d, J=7.56 Hz), 6.83 (1H, d, J=2.44 Hz), 6.83-6.62 (5H, m), 5.15 (2H, s), 4.66 (2H, s), 3.80 (3H, s), 2.24 (3H, s)

13C NMR (100 MHz, CDCl3) δ 168.94, 168.43, 159.04, 152.64, 151.86, 134.80, 129.08, 128.87, 126.41, 124.75, 123.78, 112.66, 102.82, 101.65, 82.57, 72.34, 65.12, 52.27, 14.59

QSTAR (Applied Biosystems/MDS SCIEX) (ESI): m/z 464.0930 [MH+] C25H20O7S: 465.1008, found: 465.1004

(3) Synthesis of Monoalkyl Azidomethyl Fluorescein (Compound 3 of FIG. 2)

The monoalkyl thiomethyl fluorescein (Compound 2 of the FIG. 2) (164 mg, 350 μmol) was dissolved in dichloromethane (7 ml). Subsequently, N-chlorosuccinimide (51.8 mg, 390 μmol) and trimethyl methyl silyl chloride (42.0 mg, 390 μmol) were added to the solution, and the obtained mixture was then stirred for 1 hour. Thereafter, the reaction was terminated with an $Na_2CO_3$ aqueous solution. Liquid separation was carried out with $CHCl_3$ twice, and an organic layer was then concentrated, followed by vacuum drying. The residue was dissolved in DMF (7 ml), and sodium azide (34.4 mg, 530 mmol) dissolved in 3.5 ml of $H_2O$ was then added thereto. The obtained mixture was stirred at room temperature for 1 hour. The reaction was terminated with an $Na_2CO_3$ aqueous solution. Liquid separation was carried out with AcOEt twice, and an organic layer was then concentrated. The resultant was purified by flash column chromatography (hexane/AcOEt from 5:1 to 3:2 (v/v) with 0.5% triethylamine). The obtained monoalkyl azidomethyl fluorescein (Compound 3 of FIG. 2) was in the form of a yellow crystal (71.3 mg, 44%).

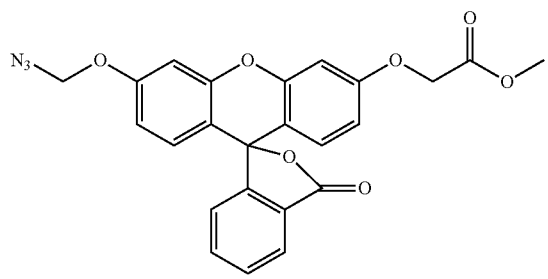

1H NMR (400 MHz, CDCl3) δ8.02 (1H, d, J=7.80 Hz), 7.65 (2H, dt, J=15.2, 14.9 Hz), 7.16 (1H, d, J=7.32 Hz), 6.90 (1H, d, J=2.20 Hz), 6.76-6.63 (5H, m), 5.18 (2H, s), 4.66 (2H, s), 3.82 (3H, s)

13C NMR (100 MHz, CDCl3) δ 169.02, 168.54, 157.87, 152.64, 152.76, 152.08, 134.95, 129.70, 129.27, 126.46, 124.95, 123.80, 111.79, 103.26, 101.80, 82.46, 79.43, 65.27, 52.42

QSTAR (Applied Biosystems/MDS SCIEX) (ESI): [MH+] C24H17N3O7: 460.1145, found: 460.1134

(4) Synthesis of Monoalkyl Azidomethyl Fluorescein

The monoalkyl azidomethyl fluorescein (Compound 3 of FIG. 2) (27.8 mg, 60 μmol) was dissolved in methanol (605 μl), and 1 M NaOHaq. (66.6 μl, 66.6 μmol) was then added to the solution. The obtained mixture was stirred for 1 hour. Thereafter, the reaction was terminated with 0.1 M HCl. Liquid separation was carried out with AcOEt twice, and an organic layer was then concentrated. The resultant was purified by flash column chromatography (CHCl3/MeOH from 30:1 to 20:1 (v/v) with 0.5% triethylamine). The obtained monoalkyl azidomethyl fluorescein (the compound as shown below) was in the form of a yellow crystal (28.2 mg, 105%).

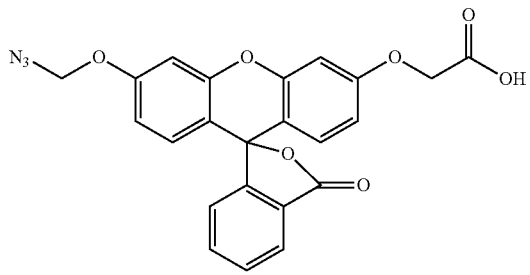

1H NMR (400 MHz, CDCl3) δ8.01 (1H, d, J=7.32 Hz), 7.64 (2H, dt, J=14.9, 15.2 Hz), 7.16 (1H, d, J=7.56 Hz), 6.88 (1H, d, J=2.20 Hz), 6.82 (1H, d, J=2.20 Hz), 6.73-6.63 (4H, m), 5.18 (2H, s), 4.51 (2H, s)

13C NMR (100 MHz, CDCl3) δ 173.69, 169.17, 157.76, 152.79, 152.30, 134.83, 129.23, 128.61, 126.62, 124.82, 123.91, 112.30, 103.22, 101.74, 82.50, 79.41, 67.57

QSTAR (Applied Biosystems/MDS SCIEX) (ESI): m/z 445.0910 [MH+] C23H15O7N3: 446.0988, found: 468.0808

(5) Azidomethyl Fluorescein NHS Ester (Compound 4 of FIG. 2)

The monoalkyl azidomethyl fluorescein (4.60 mg, 10.3 μmol) obtained in (4) above and N-hydroxysuccinimide (1.30 mg, 11.4 μmol) were dissolved in DMF (205 μl), and DCC (2.35 mg, 11.4 μmol) was then added to the solution. The obtained mixture was stirred at room temperature for 48 hours. The precipitated crystals were filtrated with a filter, and the residue was directly used in coupling with 3' amino DNA.

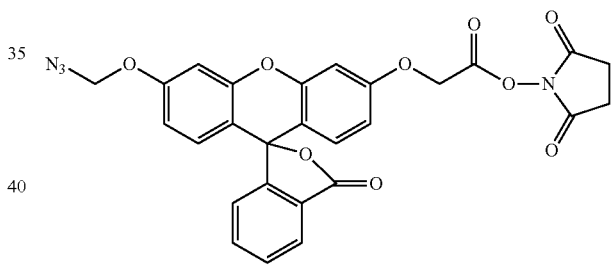

Example 2

Organic Synthesis of Bismethyl Azido Derivative of Fluorescein (1) Synthesis of Iodofluorescein (Compound 5 of FIG. 2)

Fluorescein (1.60 g, 4.61 mmol) was dissolved in 12 N HCl (16.4 ml) and 8.2 g of ice. A sodium nitrite aqueous solution (397 mg, 5.76 mmol, 8.2 ml) was slowly added to the solution, and the obtained mixture was then stirred for 2.5 hours. Thereafter, a potassium iodide aqueous solution (15.3 g, 92.2 mmol, 13.2 ml) was slowly added to the solution, and the temperature of the reaction solution was then gradually returned to room temperature. After completion of the reaction for 5 hours, the reaction was terminated with $CHCl_3$, and liquid separation was then carried out with $H_2O$ and brine. An organic layer was dried over $Na_2SO_4$, and the residue was then purified by flash column chromatography (silica, gradient elution 10:1 hexane/AcOEt to 3:1 hexane/AcOEt (v/v) with 0.5% triethylamine). The obtained iodofluorescein (Compound 5 of FIG. 2) was in the form of a yellow crystal (1 g, 47%).

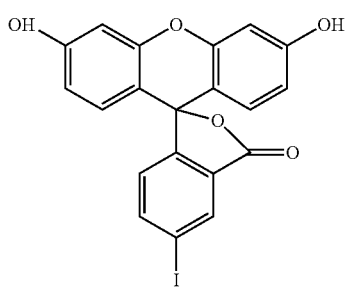

1H NMR (400 MHz, CD3OD) δ8.33-8.31 (1H, m), 8.08-8.04 (1H, m), 7.00-6.96 (1H, m), 6.67-6.50 (4H, m)

13C NMR (100 MHz, CD3OD) δ 169.5, 161.3, 153.9, 145.1, 134.7, 130.3, 130.0, 127.1, 113.6, 110.7, 103.5, 95.6

QSTAR (Applied Biosystems/MDS SCIEX) (ESI): m/z 457.9651 [MH+] C20H11IO5: 458.9729, found: 458.9721

(2) Synthesis of Trimethylfluorescein (Compound 6 of FIG. 2)

The iodofluorescein (Compound 5 of FIG. 2) (1 g, 2.18 mmol) was dissolved in anhydrous CH3CN (36 ml) in an Ar atmosphere. Silver oxide (1.52 g, 6.55 mmol), chloromethyl methyl sulfide (550 µl, 6.55 mmol) and five drops of pyridine were added to the reaction solution, and the obtained mixture was then stirred at 40° C. for 24 hours. Thereafter, the reaction solution was filtrated with Celite and was concentrated, and the resultant was then purified by flash column chromatography (hexane/AcOEt from 10:1 to 3:1 (v/v) with 0.5% triethylamine). The obtained trimethylfluorescein (Compound 6 of FIG. 2) was in the form of a yellow crystal (234 mg, 19%).

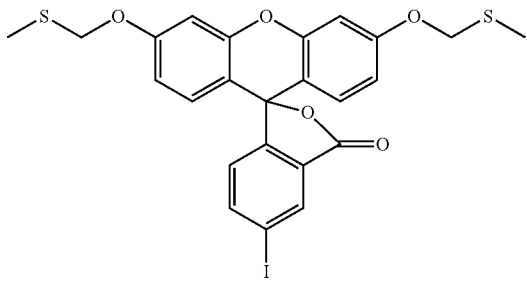

1H NMR (400 MHz, CDCl3) δ 8.35 (1H, s), 7.96 (1H, d, J=8.1 Hz), 6.92 (1H, d, J=8.3 Hz), 6.83 (2H, d, J=2.2 Hz), 6.73-6.65 (4H, m), 5.16 (4H, s), 2.26 (6H, s)

13C NMR (100 MHz, CDCl3) δ 167.3, 158.6, 152.2, 152.0, 143.6, 133.9, 128.9, 128.6, 125.6, 112.9, 111.3, 103.0, 94.9, 83.1, 72.5, 14.8

QSTAR (Applied Biosystems/MDS SCIEX) (ESI): m/z 577.9719 [MH+] C24H19IO5S2: 578.9797, found: 578.9775

(3) Synthesis of Azidomethyl Fluorescein (Compound 7 of FIG. 2)

The trimethylfluorescein (Compound 6 of FIG. 2) (200 mg, 350 mmol) was dissolved in dichloromethane (7 ml). Subsequently, N-chlorosuccinimide (102 mg, 760 µmol) was added to the solution, and the obtained mixture was then stirred at room temperature for 2 hours. Thereafter, trimethylsilyl chloride (97.3 µl, 760 µmol) was added to the reaction solution, and the obtained mixture was then stirred for 6 hours. Thereafter, the reaction was terminated with an Na2CO3 aqueous solution. Liquid separation was carried out with CHCl3 twice, and an organic layer was then concentrated, followed by vacuum drying. The residue was dissolved in DMF (7 ml), and sodium azide (67.5 mg, 1.04 mmol) dissolved in 3.5 ml of H2O was then added to the solution. The obtained mixture was stirred at room temperature for 30 hours. Thereafter, the reaction was terminated with an Na2CO3 aqueous solution. Liquid separation was carried out with AcOEt twice, and an organic layer was then concentrated. The resultant was purified by flash column chromatography (hexane/AcOEt from 10:1 to 3:1 (v/v) with 0.5% triethylamine). The obtained azidomethyl fluorescein (Compound 7 of FIG. 2) was in the form of a yellow crystal (41.0 mg, 21%).

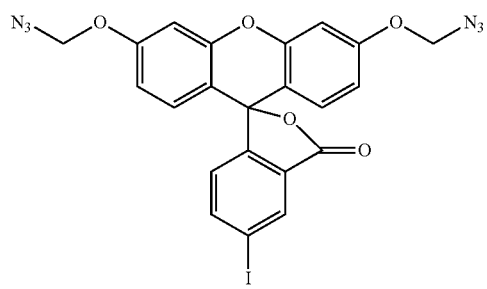

1H NMR (400 MHz, CDCl3) δ 8.36 (1H, s), 7.99-7.97 (1H, m), 6.94-6.90 (3H, m), 6.77-6.70 (4H, m), 5.19 (4H, s)

13C NMR (100 MHz, CDCl3) δ 167.3, 158.1, 152.1, 152.0, 143.7, 134.0, 129.2, 128.5, 125.5, 112.7, 112.3, 103.4, 95.0, 82.6, 79.4

QSTAR (Applied Biosystems/MDS SCIEX) (ESI): m/z 567.9992 [MH+] C22H13IN6O5: 569.0070, found: 569.0065

(4) Synthesis of Bromoacetyl Acetylene Linker

Propargylamine (116.28 µl, 1.82 mmol) and potassium carbonate (251 mg, 1.82 mmol) were dissolved in benzene (18.2 ml) in an ice water bath. Bromoacetyl bromide (159 µl, 1.82 mmol) was added to the solution, and the obtained mixture was then stirred for 20 hours. Liquid separation was carried out with ether/H2O twice, and an organic layer was then concentrated. The residue (118 mg, 37.1%) was directly used in the subsequent reaction.

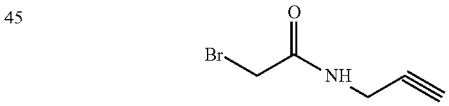

QSTAR (Applied Biosystems/MDS SCIEX) (ESI): m/z 174.9633 [MH+] C5H6BrNO: 175.9711, found: 175.9703

(5) Synthesis of Azidomethyl Bromoacetyl Linker Fluorescein (Compound 8 of FIG. 2)

Azidomethyl fluorescein (Compound 7 of FIG. 2) (50 mg, 88 µmol) was dissolved in THF (1.6 ml). Tetrakis(triphenylphosphiine)palladium (10.2 mg, 8.8 µmol), copper iodide (3.35 mg, 1.8 µmol), and triethylamine (61.9 µl, 440 µmol) were added to the solution, and finally, a bromoacetyl acetylene linker (77.0 mg, 440 µmol) was added thereto. The obtained mixture was stirred for 3 hours. The precipitated compound was removed by filtration with a filter, and the residue was then purified by flash column chromatography (hexane/AcOEt from 5:1 to 1:1 (v/v) with 0.5% triethylamine). The obtained azidomethyl bromoacetyl linker fluorescein (Compound 8 of FIG. 2) was in the form of a yellow crystal (20 mg, 37%).

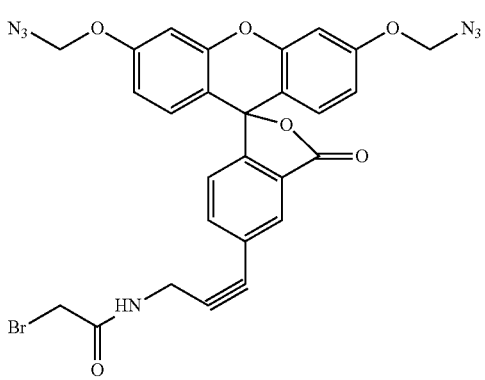

1H NMR (400 MHz, CDCl3) δ 8.06 (1H, s), 7.70 (1H, d, J=8.04), 7.27 (2H, s), 7.11 (1H, d, J=8.1), 6.91 (2H, d, J=2.2), 6.77-6.69 (4H, m), 5.19 (4H, s), 4.36 (2H, d, J=5.6), 3.94 (1H, s), 3.76 (1H, s)

13C NMR (100 MHz, CDCl3) δ 168.1, 166.6, 158.0, 152.3, 152.0, 138.2, 131.8, 129.2, 128.3, 123.9, 113.0, 112.6, 112.5, 103.4, 86.7, 82.5, 81.8, 79.4, 30.9, 28.8

QSTAR (Applied Biosystems/MDS SCIEX) (ESI): m/z 615.0502 [MH+] C27H18BrN7O6: 616.0580, found: 616.0578

Example 3

Measurement of Fluorescence Intensity

The fluorescent properties of the monomethyl azido derivative (Compound 4 of FIG. 2) and bismethyl azido derivative (Compound 8 of FIG. 2) of fluorescein, which were obtained in Example 1 and Example 2, were analyzed. The monomethyl azido derivative (Compound 4 of FIG. 2) and the bismethyl azido derivative (Compound 8 of FIG. 2) were both nonfluorescent compounds. These compounds were treated with reducing agents (Compound 4: reaction with 100 mM dithiothreitol at room temperature for 2 hours; Compound 8: reaction with tris(carboxymethyl)phosphine at room temperature for 1 hour). As a result, the azido group was converted to a hydroxyl group, and a high fluorescent property was exhibited. When compared with the compounds before the treatment, fluorescent intensity was increased by a factor of approximately 300 (Compound 4 of FIG. 2) and by a factor of approximately 2600 (Compound 8 of FIG. 2) (FIG. 3).

Example 4

Synthesis of Oligonucleotides

Oligonucleotides having the nucleotide sequences shown in FIG. 6A (also shown in SEQ ID NOS: 1 to 3 of the sequence listing) were synthesized according to a common phosphoroamidite method employing a DNA automatic synthesizer (H-8-SE; Gene World) using a 0.2 μM scale column. Deprotection of nucleotides and cleavage from a CPG carrier were carried out by incubation in an ammonia water at 55° C. for 4 hours. Oligonucleotides were purified using a reverse phase column (MicroPure II; Biosearch Technologies). The concentration was determined by measuring UV absorbance.

Example 5

Synthesis of 5' Triphenylphosphine-Linked DNA

A triphenylphosphine group was added by allowing it to react with 5' amino-modified oligo. The 5' amino-modified oligo was synthesized using 5' amino-modifier 5 (Glen Research). The reaction was carried out by intensively stirring at room temperature for 3 hours a mixed solution containing 8 mM triphenylphosphine NHS ester (in DMF), 50 mM sodium tetraborate buffer, and 200 μM 5' amino-modified oligo solution (the DMF concentration in the reaction solution: 46%). The reaction product was recovered by ethanol precipitation, and it was then purified by reverse phase HPLC (gradient conditions: 0%-50% acetonitrile/50 mM triethylammonium acetate). In addition, it was confirmed by ESI-TOF mass spectrometry that a product of interest could be obtained.

Example 6

Synthesis of 3' Azidomethyl fluorescein-Linked DNA

Azidomethyl fluorescein NHS ester (Compound 4 of FIG. 2) was added by allowing it to react with 3' phosphorothioate DNA. The 3' phosphorothioate oligo was synthesized by coupling an initial monomer with 3'-phosphate CPG, and then phosphorothioating it using a sulfurizing reagent (Glen research). The reaction was carried out by intensively stirring at room temperature for 5 hours a mixed solution containing 3 mM bromoacetylamido-Rh110-azido (in DMF), 80 mM triethylammonium bicarbonate buffer, and 300 μM 3' phosphorothioate oligo solution (the DMF concentration in the reaction solution: 80%). The reaction product was recovered by ethanol precipitation, and it was then purified by reverse phase HPLC (gradient conditions: 0%-80% acetonitrile/50 mM triethylammonium acetate). In addition, it was confirmed by ESI-TOF mass spectrometry that a product of interest could be obtained. Addition of the azidomethyl bromoacetyl linker fluoresein (Compound 8 of FIG. 2) was carried out by the same above method.

Example 7

Reaction on DNA Template and Fluorescence Measurement

A reaction on a DNA template was carried out by reacting 500 nM each of DNA template, 5' triphenylphosphine-linked probe and 3' azidomethyl fluorescein-linked probe in a buffer (20 mM Tris-HCl, 100 mM MgCl₂ 6H₂O, 0.01 mg/ml BSA; pH 7.2) at 37° C. Fluorescence signals were analyzed using a spectrophotofluorometer (FP-6500; JASCO). Fluorescence was measured every 30 seconds. The excitation wavelength was set at 490 nm, and the fluorescence wavelength was set at 520 nm.

In order to confirm target-sequence-specific signal generation, a change in a fluorescence signal over time was measured even in the absence of the target sequence, and both results were then compared with each other. As a result, in the case of the present probe, the fluorescence signal was significantly increased in the presence of the target sequence. On the other hand, such an increase in the fluorescence signal was hardly observed in the absence of the target sequence (FIG. 6B: monomethyl azido derivative (Compound 4 of FIG. 2); FIG. 6C: bismethyl azido derivative (Compound 8 of FIG. 2)). Thus, it became clear that the present probe generates a fluorescence signal in a target sequence-specific manner. In addition, the present probe enabled the discrimination of single nucleotide polymorphism (SNP) (FIG. 6D).

Example 8

Measurement of Turn Over Number

A turn over number was measured by adding 5 nM (0.1 equivalent with respect to the probe), 0.5 nM (0.01 equivalent with respect to the probe), and 0.05 nM (0.001 equivalent with respect to the probe) DNA template to 50 nM each of 5' triphenylphosphine-linked probe and 3' azidomethyl fluorescein-linked probe, and then reacting them in a buffer (20 mM Tris-HCl, 100 mM $MgCl_2\ 6H_2O$, 0.01 mg/ml BSA; pH 7.2) at 37° C. Fluorescence signals were analyzed using a spectrophotofluorometer (FP-6500; JASCO). Fluorescence was measured every 30 seconds. The excitation wavelength was set at 490 nm, and the fluorescence wavelength was set at 520 nm. The measurement was carried out for 4 hours. Four hours later, from each fluorescence signal, the amount of substance as a hydroxyl group was obtained. The obtained value was divided by the amount of substance as a template, so as to obtain a turn over number. The measurement results are shown in FIG. 7.

Actually, when the concentration of a target sequence was decreased to create turn over conditions, a turn over number of approximately 50 was obtained. Accordingly, it was found that the present fluorescence production system enables signal amplification of a factor of approximately 50 under isothermal conditions (FIG. 7).

Example 9

Detection of RNA in HL60 Cells (Fluorescence Microscope, FACS)

HL60 cells cultured in an RPMI-1640 medium were washed with Mg- and Ca-free PBS twice. Thereafter, 300 μL of 50 U/ml streptolysin O (SLO; Sigma-Aldrich) was added to the thus washed cells in each chamber, and the obtained mixture was then incubated at room temperature for 15 minutes. For this incubation, SLO had been incubated in 100 mM DTT for 2 hours, so that it had been sufficiently activated and then used. After completion of the incubation for 15 minutes, each of the probes shown in FIG. 8 (SEQ ID NOS: 4 to 7) and FIG. 9 (SEQ ID NOS: 8 to 19) was added to the resultant to a concentration of 100 nM. The obtained mixture was further incubated for 5 minutes. Thereafter, 300 uL of an MEM medium containing 0.2 g/L $CaCl_2$ was added to each well, so as to inactivate the SLO. The resultant was further incubated at 4° C. for 1 hour. Thereafter, the detected cells were photographed using a filter (excitation: 470/40; fluorescence 525/50) under a fluorescence microscope (Zeiss). Likewise, detection using a flow cytometer (Beckman Coulter) was also carried out. The results are shown in FIG. 8 and FIG. 9. As a result, RNA could be detected in the cells.

INDUSTRIAL APPLICABILITY

Applying the fluorescence-producing molecule system according to the present invention, a labeling reagent for detecting a biologically-relevant substance can be provided.

BRIEF DESCRIPTION OF THE DRAWINGS

FIG. 1 shows the on-off type fluorescence sensor system of the present invention, which produces a fluorescence as a result of the structural change of a nonfluorescent molecule triggered by reduction of a methylazido group.

FIG. 2 shows an organic synthesis scheme of a fluorescein derivative.

FIG. 3 shows the results of the measurement of the fluorescence of the fluorescein derivative of the present invention.

FIG. 4 shows a summary of the gene detection according to the present invention.

FIG. 5 shows the chemical amplification of a fluorescence signal.

FIG. 6 shows the results of a reaction on a DNA template and fluorescence measurement. FIG. 6A discloses SEQ ID NOS 1-3, respectively, in order of appearance.

FIG. 7 shows the signal amplification of the fluorescent molecule of the present invention.

FIG. 8 shows the detection of 28SrRNA in HL60 cells. (A-D) show the merge of a fluorescence image with a bright-field image, using full-match probes (A and B) and probes of scramble sequences (C and D). A and C show fluorescence images, and B and D show merges with bright-field images. (E) shows a histogram obtained by flow cytometry. The horizontal axis indicates fluorescence intensity, and the longitudinal axis indicates the number of cells. FIG. 8 discloses SEQ ID NOS 4-7, respectively, in order of appearance.

FIG. 9 shows the detection of β-actin mRNA in HL60 cells. (A-D) show the merge of a fluorescence image with a bright-field image, using full-match probes (A and B) and probes of scramble sequences (C and D). A and C show fluorescence images, and B and D show merges with bright-field images. (E) shows a histogram obtained by flow cytometry. The horizontal axis indicates fluorescence intensity, and the longitudinal axis indicates the number of cells. FIG. 9 discloses SEQ ID NOS 8-19, respectively, in order of appearance.

---

The invention claimed is:
1. A compound represented by the following formula (1) or (2):

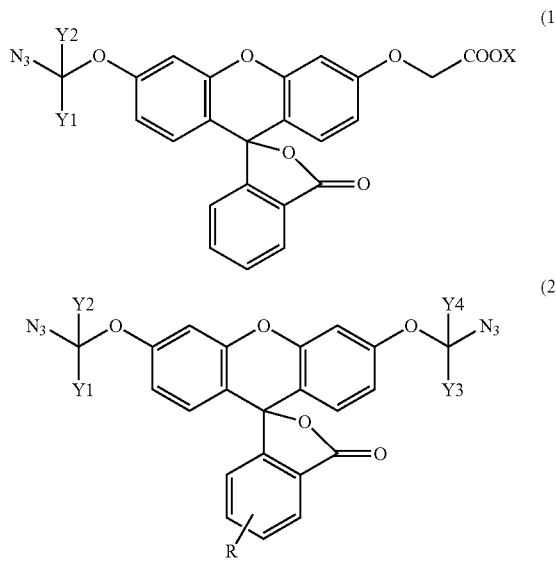

wherein X represents a hydrogen atom, or a protecting group for carboxylic acid; R represents a hydrogen atom, a halogen atom, or a reactive group that binds to a nucleic acid; and each of Y1, Y2, Y3, and Y4 independently represents a hydrogen atom, an alkyl group containing 1 to 6 carbon atoms, an alkoxy group containing 1 to 6 carbon atoms, an aryl group containing 6 to 10 carbon atoms, or a cyano group.

2. A labeling reagent for detecting a biologically-relevant substance, which comprises a composition comprising the compound according to claim 1.

3. The reagent according to claim 2, which further comprises a reducing agent.

4. A method for detecting a target nucleic acid sequence, which comprises: a step of hybridizing to a target nucleic acid sequence, a first nucleic acid probe having a nucleic acid sequence complementary to a region of a portion of the target nucleic acid sequence, which is labeled with a nonfluorescent molecule having a skeleton selected from among a fluorescein skeleton, a xanthene skeleton, a resorufin skeleton, a coumarin skeleton, an indole skeleton and a quinazoline skeleton and having a group represented by —O—C(Y1)(Y2)-N₃ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group, in the molecule, and a second nucleic acid probe having a nucleic acid sequence complementary to a region of another portion of the target nucleic acid sequence, which is labeled with a reducing agent; and a step of detecting a fluorescence produced by reducing the group represented by —O—C(Y1)(Y2)-N₃ of the nonfluorescent molecule in the first nucleic acid probe to a hydroxyl group or an oxo group.

5. The method according to claim 4, wherein a nonfluorescent molecule having a fluorescein skeleton and also having a group represented by —O—C(Y1)(Y2)-N₃ wherein each of Y1 and Y2 represents a hydrogen atom, an alkyl group containing 1 to 6 carbon atoms, an alkoxy group containing 1 to 6 carbon atoms, an aryl group containing 6 to 10 carbon atoms, or a cyano group in the molecule is used as said nonfluorescent molecule.

6. The method according to claim 4, wherein the nonfluorescent molecule is a compound represented by the following formula (1) or (2):

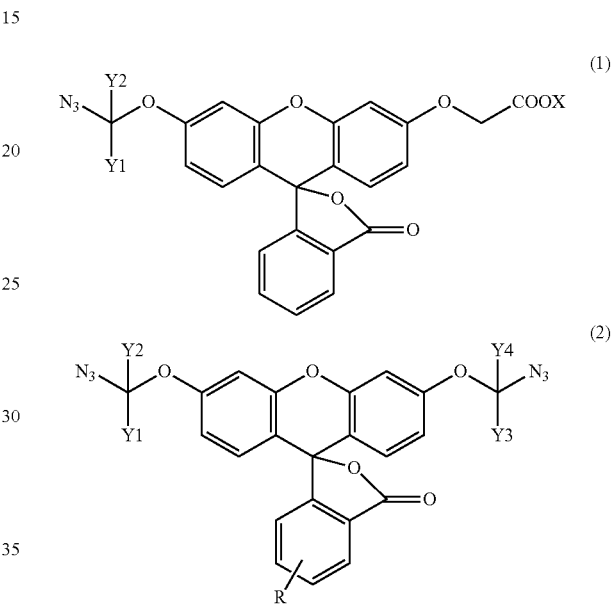

wherein X represents a hydrogen atom, or a protecting group for carboxylic acid; R represents a hydrogen atom, a halogen atom, or a reactive group that binds to a nucleic acid; and each of Y1, Y2, Y3, and Y4 independently represents a hydrogen atom, an alkyl group containing 1 to 6 carbon atoms, an alkoxy group containing 1 to 6 carbon atoms, an aryl group containing 6 to 10 carbon atoms, or a cyano group.

7. The method according to claim 4, wherein the target nucleic acid sequence is RNA.

8. The method according to claim 4, wherein single nucleotide polymorphism of the target nucleic acid sequence is detected.

9. The method according to claim 4, wherein the target nucleic acid sequence in a cell is detected.

10. The method according to claim 9, wherein a fluorescence is detected by flow cytometry, and a cell emitting a fluorescence is selected.

* * * * *